(12) United States Patent
Shimp et al.

(10) Patent No.: US 7,988,733 B2
(45) Date of Patent: Aug. 2, 2011

(54) BIOIMPLANT WITH NONUNIFORMLY CONFIGURED PROTRUSIONS ON THE LOAD BEARING SURFACES THEREOF

(75) Inventors: Lawrence A. Shimp, Morganville, NJ (US); John Winterbottom, Jackson, NJ (US)

(73) Assignee: Warsaw Orthopedic, Inc, Warsaw, IN (US)

( * ) Notice: Subject to any disclaimer, the term of this patent is extended or adjusted under 35 U.S.C. 154(b) by 77 days.

(21) Appl. No.: 11/292,809

(22) Filed: Dec. 2, 2005

(65) Prior Publication Data

US 2006/0149376 A1    Jul. 6, 2006

Related U.S. Application Data

(63) Continuation of application No. PCT/US2004/017540, filed on Jun. 3, 2004.

(60) Provisional application No. 60/475,805, filed on Jun. 3, 2003.

(51) Int. Cl.
*A61F 2/44* (2006.01)
(52) U.S. Cl. ................................. 623/17.11
(58) Field of Classification Search .............. 606/76–78; 623/17.11–17.16, 1.39, 1.4, 23.28, 23.29, 623/23.36, 23.5, 23.55, 23.6, 23.74
See application file for complete search history.

(56) References Cited

U.S. PATENT DOCUMENTS

| | | | |
|---|---|---|---|
| 4,865,603 A | 9/1989 | Noiles | |
| 4,960,425 A | 10/1990 | Yan et al. | |
| 5,011,494 A | 4/1991 | Von Recum et al. | |
| 5,609,635 A * | 3/1997 | Michelson | 623/17.16 |
| 5,989,289 A * | 11/1999 | Coates et al. | 623/17.16 |
| 6,005,164 A * | 12/1999 | Johansson et al. | 623/23.55 |
| 6,019,792 A * | 2/2000 | Cauthen | 623/17.14 |
| 6,080,193 A * | 6/2000 | Hochshuler et al. | 623/17.16 |
| 6,245,108 B1 * | 6/2001 | Biscup | 623/17.11 |
| 6,371,988 B1 * | 4/2002 | Pafford et al. | 623/17.11 |
| 6,468,311 B2 * | 10/2002 | Boyd et al. | 623/17.16 |
| 6,511,509 B1 | 1/2003 | Ford et al. | |
| 6,554,867 B1 * | 4/2003 | Joos | 623/23.5 |
| 6,569,168 B2 | 5/2003 | Lin | |
| 6,620,196 B1 * | 9/2003 | Trieu | 623/17.16 |
| 6,666,866 B2 | 12/2003 | Martz et al. | |
| 6,746,454 B2 | 6/2004 | Winterbottom et al. | |
| 6,911,045 B2 | 6/2005 | Shimp | |
| 2001/0039454 A1 * | 11/2001 | Ricci et al. | 623/23.5 |
| 2002/0026242 A1 * | 2/2002 | Boyle et al. | 623/17.11 |
| 2003/0009224 A1 * | 1/2003 | Kuras | 623/17.16 |
| 2003/0069640 A1 * | 4/2003 | Ferreira et al. | 623/17.11 |
| 2003/0093153 A1 * | 5/2003 | Banick et al. | 623/17.11 |
| 2003/0130667 A1 | 7/2003 | Lin | |
| 2003/0139813 A1 * | 7/2003 | Messerli et al. | 623/17.11 |
| 2003/0149438 A1 * | 8/2003 | Nichols et al. | 606/99 |
| 2004/0030387 A1 * | 2/2004 | Landry et al. | 623/16.11 |
| 2004/0098129 A1 | 5/2004 | Lin | |
| 2004/0133279 A1 * | 7/2004 | Krueger et al. | 623/17.16 |
| 2004/0162562 A1 | 8/2004 | Martz | |

(Continued)

FOREIGN PATENT DOCUMENTS

WO    WO 01/08611    2/2001

(Continued)

*Primary Examiner* — Nicholas Woodall

(57) ABSTRACT

A bioimplant is configured with at least two load-bearing surfaces each having a plurality of protrusions oriented at an angle with respect to one another to resist translation in all directions when opposing load bearing surfaces are under normally applied compressive loads.

17 Claims, 2 Drawing Sheets

U.S. PATENT DOCUMENTS

| | | |
|---|---|---|
| 2004/0172130 A1* | 9/2004 | Nakahara et al. ........... 623/17.11 |
| 2004/0181286 A1* | 9/2004 | Michelson ................... 623/23.5 |
| 2004/0243242 A1 | 12/2004 | Sybert et al. |
| 2004/0249377 A1 | 12/2004 | Kaes et al. |
| 2005/0027360 A1* | 2/2005 | Webb et al. ................. 623/17.11 |
| 2005/0038511 A1 | 2/2005 | Martz et al. |
| 2005/0209698 A1* | 9/2005 | Gordon et al. ............. 623/17.15 |
| 2005/0240188 A1 | 10/2005 | Chow et al. |
| 2005/0251146 A1 | 11/2005 | Martz et al. |
| 2006/0095043 A1 | 5/2006 | Martz et al. |
| 2007/0073293 A1 | 3/2007 | Martz et al. |
| 2007/0100452 A1* | 5/2007 | Prosser ...................... 623/17.11 |

FOREIGN PATENT DOCUMENTS

| | | |
|---|---|---|
| WO | WO 02/067956 | 8/2002 |
| WO | WO 02/087654 A2 * | 11/2002 |

\* cited by examiner

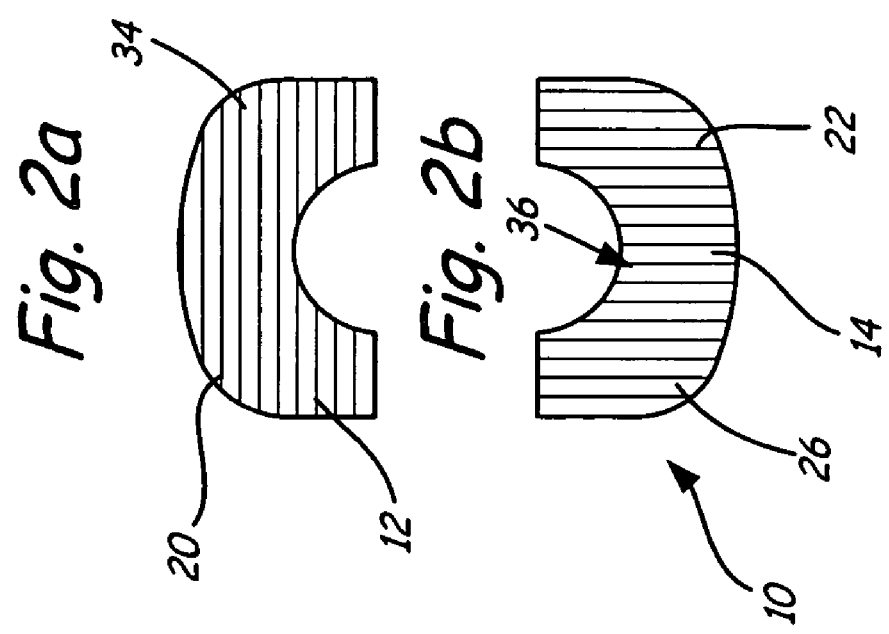
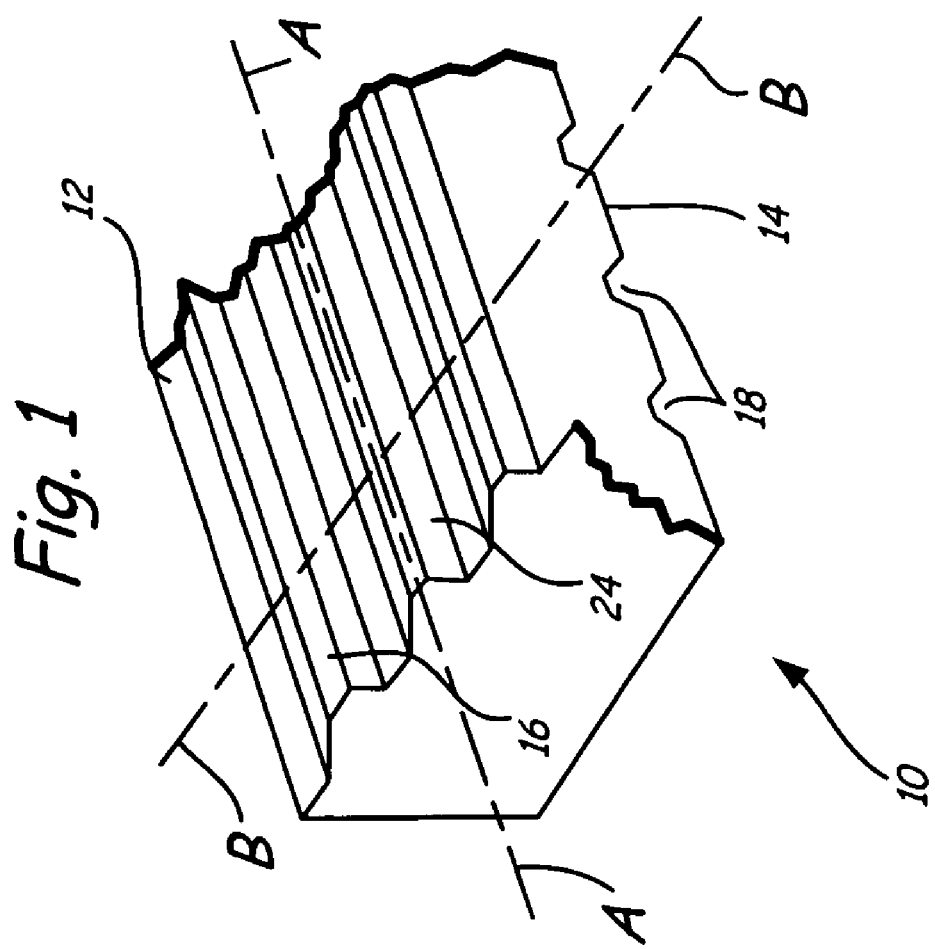

BIOIMPLANT WITH NONUNIFORMLY CONFIGURED PROTRUSIONS ON THE LOAD BEARING SURFACES THEREOF

CROSS-REFERENCE TO RELATED APPLICATIONS

This application is a continuation of International Patent Application No. PCT/US2004/017540, filed on Jun. 3, 2004, which claims the benefit of U.S. Provisional Application Ser. No. 60/475,805, filed Jun. 3, 2003, the contents of both applications are incorporated by reference herein.

BACKGROUND OF THE INVENTION

1. Field of the Invention

This invention is generally directed toward a surgical bioimplant. Particularly, the invention relates to the geometry of the bioimplant's load bearing surfaces configured to improve resistance of the bioimplant to omnidirectional translations at the surgical site.

2. Description of the Prior Art

Spinal fusion is directed to provide stabilization of the spinal column for painful spinal motion and disorders such as structural deformity, traumatic instability, degenerative instability, and post-resection instability. Fusion, or arthrodesis, is achieved by the formation of an osseous bridge between adjacent motion segments. This can be accomplished within the disc space, anteriorly between contiguous vertebral bodies or posteriorly between consecutive transverse processes, laminae or other posterior aspects of the vertebrae.

A fusion or arthrodesis procedure is often performed to treat an anomaly involving an intervertebral disc. Intervertebral discs, located between the endplates of adjacent vertebrae, stabilize the spine, distribute forces between vertebrae and cushion vertebral bodies. A normal intervertebral disc includes a semi-gelatinous component, the nucleus pulposus, which is surrounded and confined by an outer, fibrous ring called the annulus fibrosis. In a healthy, undamaged spine, the annulus fibrosis prevents the nucleus pulposus from protruding outside the disc space.

Spinal discs may be displaced or damaged due to trauma, disease or aging. Disruption of the annulus fibrosis allows the nucleus pulposus to protrude into the vertebral canal; a condition commonly referred to as a herniated or ruptured disc. The extruded nucleus pulposus may press on the spinal nerve, which may result in nerve damage, pain, numbness, muscle weakness and paralysis. Intervertebral discs may also deteriorate due to the normal aging process or disease. As a disc dehydrates and hardens, the disc space height will be reduced leading to instability of the spine, decreased mobility and pain.

Sometimes the only relief from the symptoms of these conditions is a discectomy, or surgical removal of a portion or all of an intervertebral disc followed by fusion of the adjacent vertebrae. The removal of the damaged or unhealthy disc will allow the disc space to collapse. Collapse of the disc space can cause instability of the spine, abnormal joint mechanics, premature development of arthritis or nerve damage, in addition to severe pain. Pain relief via discectomy and arthrodesis requires preservation of the disc space and eventual fusion of the affected motion segments.

One of numerous solutions to the stabilization of an excised disc space is to fuse the vertebrae between their respective end plates, preferably without the need for anterior or posterior plating. There have been an extensive number of attempts to develop an acceptable implant that could be used to replace a damaged disc and maintain the stability of the disc interspace between the adjacent vertebrae, at least until complete arthrodesis is achieved. To be successful the implant must provide temporary support and allow bone ingrowth. Success of the discectomy and fusion procedure requires the development of a contiguous growth of bone to create a solid mass because the implant may not withstand the cyclic spinal loads for the life of the patient.

Many attempts to restore the intervertebral disc space after removal of the disc have relied on various bone grafts promoting osteogenesis. The use of autograpft bone (taken from the patient), allograft bone (obtained from other individual) or xenograft (bone of a different species) is well known in both human and veterinary medicine. Both allograft and autograft are biological materials which are replaced over time with the patient's own bone, via the process of creeping substitution. Over time, a bone graft virtually disappears unlike a metal implant, which persists long after its useful life. Stress shielding is avoided because bone grafts have a similar modulus of elasticity as the surrounding bone. Regardless of the type of the bone graft, it should have the following characteristics:

Tolerance to high bearing loads; and

Osteoinductivity and osteoconductivity needed for accelerating the growth of new bone tissue at the site.

Hence, compositionally, an implant advantageously has a substantial inner portion of mineralized bone and an outer portion or layer of demineralized bone providing a fusing interface with adjacent vertebrae.

However, the composition of the implant alone is not necessarily sufficient to provide a high rate of fusion. Rather, the combination of composition and geometry of the implant markedly improves its biomechanical properties. Once in situ, the osteogenic implant is exposed to multidirectional compressive loads tending to cause the implant to translate, which, in turn, may cause neural and vascular injury, as well as collapse of the disc space. Accordingly, it is imperative that the coupling between the implant and the adjacent vertebrae remain structurally sound to minimize slippage and potential expulsion of the implant. One of the consequences of relative displacement is associated with a friction between the juxtaposed surfaces of the implant and the adjacent vertebral bodies, which leads to gradual, but not uniform thinning of the demineralized layer and, thus, detrimentally affects osteoinductivity and/or osteoconductivity. Thus, among others, the design of the bioimplant should consider the following aspects:

Minimization of relative displacement between the implant and adjacent vertebrae caused by multidirectional compressive forces; and Geometry of the load bearing surfaces of the implant should minimize damage to the surface features of the implant when the implant is exposed to multidirectional translations.

These problems have been addressed, but not fully solved, by providing osteogenic implants with texturized demineralized layers. For example, U.S. Pat. No. 6,511,509 discloses a texturized bioimplant having one or more texturized bone surfaces each provided with spaced or continuous protrusions. Configured uniformly, the protrusions engage the end plate(s) of the adjacent vertebrae at a uniform angle with respect to the central axis of the implant.

U.S. Pat. No. 6,511,509 represents a typical structure of a texturized surface. Regardless of numerous shapes and dimensions, the protrusions are typically uniformly shaped, dimensioned and oriented with respect to the endplate(s) of the vertebrae and are therefore nonselective in their response to compressive forces applied against them. However, such a configuration does not take into account the fact that applied compressive loads are typically multidirectional. Accordingly, whereas one group of protrusions, for example protrusions facing the end plate of the superior vertebra, may reliably anchor the implant in one direction, the other group of protrusions located on the bottom of the implant may be not as effective. Furthermore, the pressure distribution over the entire load bearing surfaces of the implant is rarely uniform. As a consequence, some of the protrusions are exposed to higher friction forces which have been found to lead to uneven scrapping of the demineralized layer located on the outer surface of the protrusions. Hence, the osteoinductivity of the bioimplant may be detrimentally affected.

Thus, a need exists for a bioimplant having a structure configured to minimize the displacement between the bioimplant and the adjacent vertebrae and to minimize damage to the demineralized layer of the bioimplant if and when such translations occur.

SUMMARY OF THE INVENTION

It is an object of the invention to provide a bioimplant, in particular, an intervertebral implant, derived from bone and configured to minimize the effect produced by multidirectional translational loads acting thereupon at the implantation site (such as the intervertebral space between adjacent vertebrae which results form surgical removal of the intervertebral disc) so that the bioimplant does not shift, expel, rotate or incur significant damage during and/or after its implantation.

Still another object of the invention is to provide such a bioimplant configured to account for uneven distribution of forces produced by multidirectional loads at the surgical site to minimize the wear of a demineralized layer provided on the load bearing surfaces of the bioimplant.

A further object of the invention is to provide a bioimplant with load-bearing surfaces texturized to improve the implant's stability, osteoconductivity and/or osteoinductivity.

By way of achieving these and other objects of the invention, a bioimplant is provided which on implantation is subject to multidirectional translational loads tending to cause displacement of the bioimplant from the site of its implantation, the bioimplant possessing a plurality of nonuniformly configured protrusions on at least a portion of its load-bearing surfaces for selectively resisting such loads.

In accordance with one aspect of the invention, the protrusions, taken as a complete system on both load bearing surfaces of the implant, are arranged to resist lateral displacement in all directions. This may be accomplished by having different, complementary patterns of protrusions on the top and bottom load bearing surfaces, or by having similar, or identical multidirectional protrusions on each surface. An example of complementary protrusions is ridges that run parallel to reach other on a given surface, but at an angle (preferably perpendicular) when comparing one face to another. An example of multidirectional protrusions is a circular or semicircular pattern of ridges. An example of an existing multidirectional pattern is a series of pyramidal shapes, which are made by patterns of intersecting ridge lines. By nature, these patterns require at least two machining steps, to form each of the intersection grids. The preferred patterns of the present invention can be made by one machining step (using a shape, multi-point cutting tool). It is easy to see how parallel patterns or circular patterns can be made in one step. An obvious advantage of one step machining is a savings in time and part set-up.

In accordance with another aspect of the invention, the size of the protrusions on the load-bearing surfaces of the bioimplant may be varied within multiple clusters, groups or sections of the protrusions to compensate for uneven distribution of compressive loads applied in multiple directions. Even in the context of a substantially unidirectional force, some of the protrusions may be under higher stress than others due to a variety of factors associated with each given surgical site and including, among others, geometrical, topographical and force-distribution factors. Also, a bioimplant may have relatively weak regions on or beneath the load bearing surfaces due to the geometry of the implant, wherein the regions bordering with a central opening are relatively weak, or due to the inherent compositional characteristics of the bone source. Thus, depending on the vector of resulting force tending to displace the implant away from its implantation site, it is advantageous to selectively reduce the stress on those protrusions that, while providing a load-bearing support, may not be instrumental in stopping the expulsion if the implant. One of the possible modifications of the inventive implant addressing this problem is to vary the size of the protrusions within the same group. Alternatively or simultaneously with the differently sized protrusions, their shape can be varied as well. An important advantage stemming from the variously formed protrusions includes the preservation of the demineralized layer critical to the osteoinductive characteristic of the implant during fusion. Additionally, diversifying the positioning of the protrusions on the load bearing surfaces can direct the multidirectional loads away from or toward particular regions or features of the implant. This will enable implants not typically able to resist direct loads, applied evenly across their surfaces, to be used in spinal fusion. For example, should the bioimplant contain holes or weak regions due to its natural characteristics or resulting from machining or chemical treatment, the protrusions may be used to direct the load away from these areas increasing the overall load bearing efficiency of the bioimplant. The size and shape of protrusions may be also selected so that the implant conforms to the endplates of vertebral bodies thereby restoring lordosis or kyphosis and increasing the contact area between the bioimplant and the site of its implantation.

BRIEF DESCRIPTION OF THE DRAWINGS

The above and other objects, features and advantages will become more readily apparent from the specific description of the bioimplant of the invention accompanied by the following drawings, in which:

FIG. 1 is an isometric view of an embodiment of bioimplant configured in accordance with the invention;

FIGS. 2a-2b are top and bottom views, respectively of another embodiment of bioimplant configured in accordance with the invention.

DETAILED DESCRIPTION OF THE INVENTION

Figure 3A:
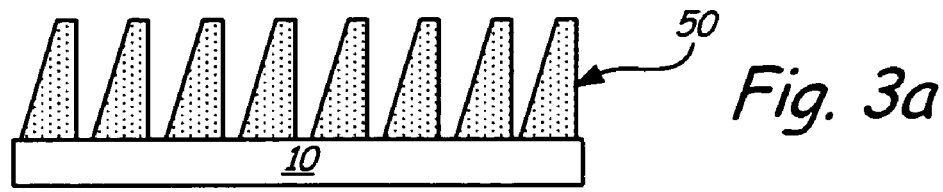
FIGS. 3a-3g illustrate differently texturized load-bearing surfaces configured in accordance with the invention.

Referring to FIGS. 1 and 2, a surgical bioimplant 10 useful as an intervertebral implant is provided with load bearing surfaces typically juxtaposed with end plates of adjacent vertebrae (not shown) and configured to improve stabilization of the implant at the surgical site by gradually fusing the bearing surfaces with the end plates. The term "bioimplant" as used herein, refers to an implant comprising cortical and/or cancellous bone, from autograft, allograft or xenograft origin, which is processed for implantation into a living patient. The term "stability" as used herein, refers to the ability of the textured bioimplant to remain at an implantation site without significantly shifting, rotating, or being extruded.

Note, however, that implant 10 may be manufactured from other suitable implant materials, which are capable of withstanding the compression and torsional loads. Among others, such material may include composites of Hydroxyapatite, calcium carbonates, calcium phosphates, calcium phosphosilicates, calcium sulfates, magnesium sterate, polyether ketones, polycaprolactones, lactide-coglycolides, polyurethanes, glass ceramic composites etc.

Referring to the bioimplant comprising cortical and/or cancellous bones, it can comprise bone in the form of fibular wedges; humeral wedges; tibial wedges; fibular trapezoid wedges; humeral trapezoid wedges; and femoral trapezoid wedges; fibular shafts and rings, humeral shafts and rings, femoral shafts and rings. In addition or alternatively, the bioimplant may be essentially intact bone grafts including for example proximal and distal femur, femoral head; and small cut bone grafts including for example cancellous cubes, iliac crest wedges, and Cloward dowels. Based on its composition, the bioimplant may be osteoinductive and/or osteoconductive. The term "osteoconductive" as used herein refers to the ability of a substance or material to provide surfaces which are receptive to the growth of new host bone. The term "osteoinductive" as used herein refers to the quality of substance or material to recruit cells from the host that have the potential to stimulate new bone formation. Any material that can induce the formation of ectopic bone in the soft tissue of an animal is considered osteoinductive. For example, most osteoinductive materials induce bone formation in athymic rats when assayed according to the method of Edwards et al. ("Osteoinduction of Human Demineralized Bone: Characterization in a Rat Model" Clinical Orthopeadics& Rel. Res., 357:219-228, December 1998; incorporated herein by reference). In other instances, osteoinduction is considered to occur through cellular recruitment and induction of the recruited cells to an osteogenic phenotype. Osteoinductivity may also be determined in tissue culture as the ability to induce an osteogenic phenotype in culture cells (primary, secondary, or explants). It is advisable to calibrate the tissue culture method with an in vivo ectopic bone formation assay as described by Zhang et al. ("A quantitative assessment of osteoinductivity of human demineralized bone matrix" J. Periodontol. 68(11):1076-84, November 1997; incorporated herein by reference). Calibration of the in vitro assays against an art-accepted in vivo ectopic bone formation model is important because the ability of a compound to induce an apparent "osteogenic" phenotype in tissue culture may not always be correlated with the induction of new bone formation in vivo. BMP, IGF, TGF-$\beta$, and angiogenic factors are among the osteoinductive factors found to recruit cells from the marrow or perivascular space to the site of injury and then cause the differentiation of these recruited cells down a pathway responsible for bone formation. DBM isolated from either bone or dentin are both osteoinductive materials (Ray et al., "Bone implants" J. Bone Joint Surgery 39A: 1119, 1957; Urist, "Bone: formation by autoinduction" Science 150:893, 1965; each of which is incorporated herein by reference).

Allograft bone tissue is obtained from a cadaver of the same species as the recipient, and processed under strict aseptic conditions in certified clean room operating suites. The bone tissue is preferably processed to remove all soft tissue, including marrow and blood, to produce a cleaned bone material suitable for bioimplant use. Suitable processing methods are well known to those skilled in the art and can be readily selected and employed by those of ordinary skill in the art without undue experimentation. Known methods of bone processing include those disclosed in, for example, U.S. Pat. No. 5,556,379, the contents of which are incorporated by reference herein. After processing, the cleaned bone materials are packaged under sterile conditions and stored for latter processing into the present texturized bioimplant, or immediately processed into the present texturized bioimplant followed by appropriate packaging. The use of fresh, fresh-frozen and/or freeze-dried bioimplants are preferred.

Bioimplant 10 has textured load-bearing surfaces 12 and 14 facing the end plates of the superior and inferior vertebrae, respectively, and configured to gradually fuse with the latter, as is known in the related art. The term "texturized bioimplant" as used herein refers to a bioimplant having one or more protrusions provided on the surface of a bioimplant where the load bearing surfaces 12 and 14 of the bioimplant can be any surface including a natural surface and/or a cut surface. The term "protrusion" as used herein, refers to an irregularity in a surface of a bioimplant. Note, as mentioned above, the entire implant 10 including the protrusions may be made entirely of the mineralized bone, or at least the outer layers of the protrusions may be made from a demineralized bone.

The protrusions do not necessarily have to be formed over an entire surface of a bioimplant. Formation of the protrusions may be limited to a portion of a surface. For example, protrusions may be patterned over the entire natural and cut surfaces of a bone or composite comprising bone, over a portion of the natural and/or cut surfaces of bone or a composite comprising bone, or over the entire cut surface of bone or a composite comprising bone.

Texturized implants 10 are useful in spinal applications including restoration of anterior column support and can be used from either an anterior, posterior or posteriolateral approach. Furthermore, texturized implants 10 are also suitable for placement in cervical, thoracic and lumbar interbody fusions and, preferably, include textured wedges, (wedges are not always needed) cubes or disks. The latter may include, but not limited to fibular textured bioimplant wedges, humeral textured bioimplant wedges, tibial textured bioimplant wedges and femoral textured bioimplant wedges. Texturized bioimplants 10 suitable for addressing large column defects include texturized bioimplant shafts, including for example fibular texturized shafts, humeral texturized shafts and femoral texturized shafts.

Texturized bioimplants 10 are preferably texturized with a plurality of closely spaced protrusions over their entire opposing cut surfaces. Other suitable grafts for cervical fusion include texturized iliac crest bioimplants or texturized cancellous implants. The present texturized implant is useful for implantation in patients suffering from defects caused by congenital anomaly, disease, or trauma, including for example, spine fractures; deformity, e.g. kyphotic deformities, e.g. posttraumatic kyphosis; postlaminectomy kyphosis, junctional kyphosis, and Scheuermann's kyphosis; scoliosis, e.g. neuromuscular scoliosis, adult scoliosis, paralytic scoliosis, congenital and syndromic scoliosis; and cervical neck pain. Surgical methods for correcting degenerative conditions, for example in the lumbar spine, include decompression, excision of disc material, hypertrophied bone, or ligament along with fusion or fusion alone. An anterior, transverse, anterolateral or posterior surgical approach can be used. The site of primary pathology and surgeon preference dictates the choice of approach. Pathology that involves vertebral bodies is best approached anteriorly through the thorax, abdomen or flank. Pathology involving posterior elements is best approached posteriorly for example, through a vertical midline approach or posterior lateral muscle spinning approach.

Orthopedic surgeons and spinal surgeons conducting a surgical implantation procedure such as tibial plateau, complete vertebral replacement, removal of shattered vertebrae etc., in which expulsion of the implant is of concern can readily select and employ a particular texturized bioimplant optimally suited for the procedure. Factors to be considered in such selection and employment include the type of bioimplant bone, its anatomic site of fusion, activity level and the age of the patient. Critically, however, the size of the texturized implant will vary according to its use and may vary to restore natural or desired positioning of the vertebrae etc.

An ideal bioimplant, used, for example, in lumbar interbody fusion, should be osteoinductive, osteoconductive, non-immunogenic, appropriately sized and shaped to provide stability. Indications, diagnostic criteria, graft selection and surgical technique are factors that can be readily selected, optimized and employed by those of ordinary skill in the art without undue experimentation. All of the above is discussed in *Master Techniques in Orthopedic Surgery, The Spine*, edited by Bradford, David S., Lippincott-Raven, ISBN 0-7817-0033-7, Philadelphia, Pa., (1997) and incorporated herein by reference in its entirety.

Protrusions 16, 18, 20 and 22 can be discrete, continuous, or a combination thereof, and can be of any shape including for example: irregular; pyramidal; conical; cuboidal; rectangular; and cylindrical; or any combination thereof. Further, a cross-section of a continuous or discrete protrusion maybe of any shape including for example: irregular; rectangular; square; oval; round; triangular; trapezoidal; and a regular or irregular curve; or any combination thereof. The protrusions can be provided on the bioimplant surface in a regular, symmetric pattern including for example a grid-type pattern, or for example, a pattern of concentric rings, or in an irregular pattern.

The expression "continuous protrusion" as used herein, refers to a protrusion whose length in a plane extending transversely to the load bearing surfaces continues substantially uninterrupted, including for example a linear or curved protrusion. The length of the protrusions is about at least three times greater than its width, but it is preferred that the length is about at least five times greater, and includes for example a continuous, protruding concentric ring, and a continuous linear protrusion in a plane extending transversely to the load bearing surfaces. Each continuous protrusion may or may not be distinct from another continuous protrusion.

The expression "discrete protrusion" as used herein, refers to a protrusion which is discontinuous, i.e. which has a distinct length and width, where each discrete protrusion is separate and distinct from every other discrete protrusion, and includes for example a protrusion whose length is less than about three times its width. Preferably, the length is less than twice its width and even more preferably, a discrete protrusion has a length which is about equal to its width.

The expression "nonuniformly configured" as applied to the protrusions defined upon the load bearing surfaces of the bioimplant of this invention refer to the differences in the pattern, arrangement, size, distance in separation, shape, cross section, etc., of the protrusions within a cluster or section of protrusions present on a load bearing surface of the bioimplant and distinguish such protrusions from the uniformly configured texturized surfaces of the implants disclosed in U.S. Pat. No. 6,511,509 discussed supra.

Critically, protrusions 16 and 18 need to provide implant 10 with a high mechanical strength capable of withstanding multidirectional loads. The expression "mechanical strength" as used herein refers to the ability of a bioimplant to withstand typical mechanical loads and stresses at an implant site without failing. The term "stress" as used herein refers to load per unit cross-sectional area.

Referring to FIGS. 1 and 2, protrusions 16 and 20 provided on load bearing surface 12, and protrusions 18 and 22 (FIGS. 1 and 2, respectively) provided on the bottom of load bearing surface 14 are angled with respect to one another. For example, as can be seen in FIG. 1, protrusions 16 lying parallel to axis A-A (FIG. 1) and protrusions 18 extending parallel to axis B-B extend in transverse planes such as coronal and sagittal planes. Although, as shown in FIGS. 1 and 2, protrusions 16 and 18 are shown to extend generally perpendicular to one another, any angle between axes A-A and B-B will successfully implement the inventive concept. Accordingly, protrusions 16 coupled to a respective end plate can effectively resist a force directed along axis B-B whereas bottom protrusions 18 resist a force directed along the axis A-A. Given only as an example, axis A-A extends, for example, in a coronal plane corresponding to an anterior/posterior direction whereas axis B-B coincides with a sagittal plane extending transversely to the coronal plane. As a consequence, bioimplant 10 can resist translation in multiple directions when the opposing load-bearing surfaces 12 and 14 are under normally applied compressive loads. Furthermore, bioimplant 10 will not tend to deviate substantially from the intended insertion path (direction of applied insertion load) while opposing surfaces 12 and 14 with the inventive protrusions features of the implant are under compressive loading.

In accordance with a further feature of the invention, adjacent regions of the same or opposing load-bearing surface 12 and 14 may be provided with differently oriented protrusions and troughs 24 formed between the protrusions. Similarly to the main concept, variously oriented groups of protrusions and troughs improve the stabilization of the implant at the surgical site minimizing undesired relative displacement between the adjacent vertebrae and the bioimplant.

In accordance with one of the auxiliary features of the invention, if the implant possesses a demineralized layer 26 (FIG. 2*b*), in order to preserve such layer from premature deterioration caused by relative displacement of the implant and the vertebrae surfaces, protrusions 30 and 32 can be nonuniformly sized. Various regions of load bearing surfaces 12 and 14 are typically exposed to unevenly distributed compressive loads and thus experience relatively low or high local stresses. Furthermore, even if the compressive loads are relatively uniform, local regions on the same surface may be weaker or stronger due to the inherent characteristics of the source of bone material for the bioimplant and/or its geometry. Typically, regions 34 and 36 (FIGS. 2*a*, 2*b*) located close to the periphery of the load bearing surfaces are relatively weak. Therefore, modifying the height of the protrusions 30, 32 (FIG. 3E) as a function of the level of the stress may reduce the deterioration of the demineralized layer (again this does not just apply to the protecting the demin layer, but also to controlling mechanical damage to the implant by directing the compressive and shear loads by selectively arranging the implant protrusions) 26 (FIG. 2*b*) typically abraded away by the end plates of the adjacent vertebrae.

The height of the protrusions 16, 18, 20 and 22 can vary, e.g., from about 0.1 to about 6.0 mm, preferably from about 0.3 to about 3.0 mm and more preferably from about 0.5 to about 1.5 mm for the reasons discussed above. Advantageously, the height of the protrusions can range from about 0.1 mm to about 5.0 mm.

Other protrusions, for example concentric rings or other curved or irregular- or regular-shaped protrusions, can be provided by attaching a drill bit having a blade corresponding to the protrusion pattern desired where the blade is appropriately sized to provide a desired protrusion width, length, and height and profile, to a drill and drilling the desired surface of the bone to achieve the desired textured surface. One of ordinary skill in the art can readily design and produce, or select, and employ an appropriate milling tool to achieve a desired textured surface on a bioimplant.

Figure 3B:
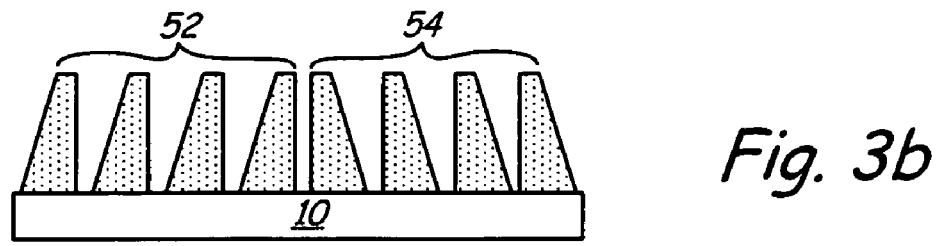
Figure 3C:
Figure 3D:
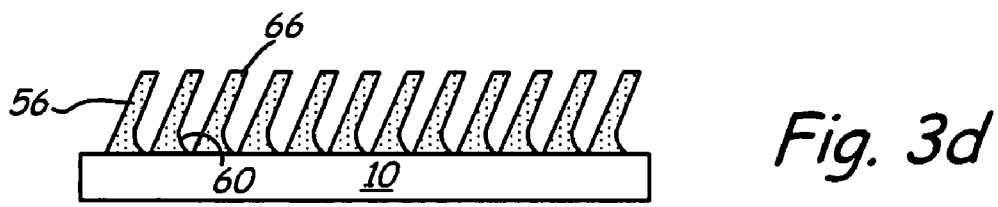
Figure 3E:
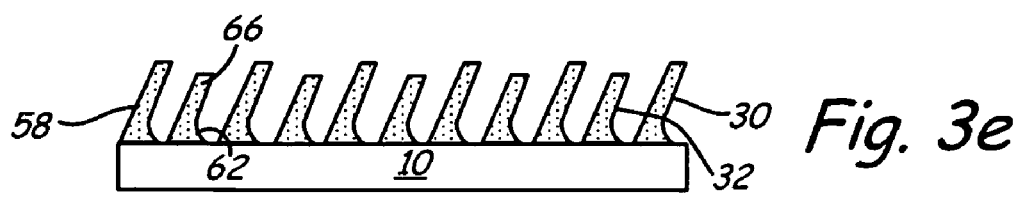
Figure 3F:
Figure 3G:
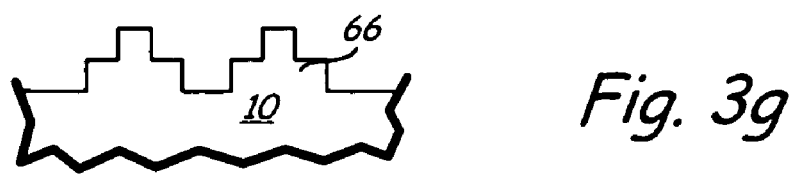

Some of the above-disclosed protrusion configurations are illustrated in FIGS. 3a-3g. Thus, for example, FIGS. 3a-3e show protrusions characterized by a generally polygonal shape differing from a triangular one. Whereas FIG. 3a illustrates uniformly oriented protrusions 50, FIG. 3b shows trapezoidal protrusions 52 and 54 grouped so that, regardless of whether they are formed on the same load-bearing surface and/or opposite surfaces, each group is angled differently. Somewhat different polygonal cross-sections are illustrated in FIGS. 3d-3e and 3g. Thus, protrusions 56 and 58 (FIGS. 3d, 3e) have portions 60 and 62, respectively, extending laterally outwardly from a body 66 to enlarge the base of the body 66 and thus to improve the resistance of the entire cluster of the protrusions to multidirectional compressive loads. Even larger area is provided by the modification shown in FIG. 3g wherein body 66 has a cascaded, or multilevel, structure having each side provided with at least two right angles. Advantageously, the protrusions are closely spaced. The expression "closely spaced" as used herein refers to protrusions which are in close proximity to each other. Preferably the protrusions are spaced no more than about 6.0 mm apart (i.e., the distance between the edges of two adjacent protrusions), more preferably no more than about 2.0 mm apart and more preferably no more than about 1.5 mm apart but in any event not less than about 0.5 mm apart. Finally, FIG. 3f illustrates a wave-like protrusion configuration.

The protrusion(s) can be formed over an entire surface of the bioimplant or over just a portion of a surface, for example, over the entire natural and cut load bearing surfaces, over a portion of the natural and/or cut surfaces, or over the entire cut surface. The protrusions can be formed on the surface in any number of ways including, for example, mechanical and/or chemical methods directed to form a series of parallel linear or curved grooves. Preferably, the bioimplant protrusions are formed by milling a first set of parallel linear groves on the cut surface of the bioimplant followed by turning the bioimplant and forming a second set of parallel grooves at an angle to the first series. Milling is preferably achieved by running the graft over a milling tool configured to have multiple closely spaced and adjustable blades on one or more surfaces to achieve a desired height and width of the protrusions on one of load bearing surfaces 12 and 14. Thereafter, upon turning the graft at, for example, a 90-degree angle, the other bearing surface is treated again in the same manner. As a result, opposing load-bearing surfaces 12 and 14 are provided the discrete protrusions. Milling can also be achieved using, for example, a routing tool, a laser and/or masking and acid etching.

What is claimed is:

1. A bioimplant which on implantation is subject to multidirectional translational loads tending to cause displacement of the bioimplant from the site of its implantation, the bioimplant comprising:

a single top load bearing surface, the top load bearing surface defined in a first plane and having a plurality of nonuniformly configured protusions extending therefrom and extending along the top load bearing surface in generally a first direction; and a single bottom load bearing surface, the bottom load bearing surface defined in a second plane and having a plurality of nonuniformly configured protrusions extending therefrom and extending along the bottom load bearing surface in one or more directions;

wherein in a superimposed view of the first and second planes, the first direction is substantially nonparallel to all of the one or more directions of the protusions extending along the bottom load bearing surface, and the protrusions are substantially nonuniformly shaped and sized, and each protrusion having a different angle relative to each other.

2. The bioimplant of claim 1 wherein the configuration of the protrusions on the load bearing surfaces is such as to resist translation of the bioimplant in all directions when the bioimplant is under translational load.

3. The bioimplant of claim 1 wherein at least some of the protrusions have a generally cascade configuration possessing at least two parallel sides.

4. The bioimplant of claim 1 wherein the load bearing surfaces are demineralized.

5. The bioimplant of claim 4 which is an intervertebral implant.

6. The bioimplant of claim 1 wherein at least some of the protrusions possess a cross section having more than three sides.

7. The bioimplant of claim 1 wherein at least some of the protrusions possess generally ovoid cross section.

8. The bioimplant of claim 1 wherein at least some of the protrusions closely spaced.

9. The bioimplant of claim 8 wherein at least some of the protrusions are spaced apart by no more than about 6.0 mm.

10. The bioimplant of claim 9 wherein at least some of the protrusions are spaced apart by from about 0.5 mm to about 1.5 mm.

11. The bioimplant of claim 1 wherein at least some of the protrusions have a height of from about 0.1 mm to about 6.0 mm.

12. The bioimplant of claim 11 wherein at least some of the protrusions have a height of from about 0.3 to about 3.0 mm.

13. The bioimplant of claim 11 wherein at least some of the protrusions have a height of from about 0.5 to about 1.5 mm.

14. The bioimplant of claim 1 wherein at least some protrusions are arranged in a generally curved pattern.

15. The bioimplant of claim 1 which is an intervertebral implant.

16. The bioimplant of claim 1, wherein in a superimposed view of the first and second planes, the first direction is generally perpendicular to substantially all of the one or more directions of the protrusions extending along the bottom load bearing surface.

17. A bioimplant which on implantation is subject to multidirectional translational loads tending to cause displacement of the bioimplant from the site of its implantation, the bioimplant comprising:

a bone derived substantially rigid structure having a single planar top load bearing surface, the top load bearing surface having a plurality of nonuniformly configured protusions extending therefrom and extending along the top load bearing surface in generally a first direction; and a single planar bottom load bearing surface, the bottom load bearing surface having a plurality of nonuniformly configured protusions extending therefrom and extending along the bottom load bearing surface in one or more directions;

wherein in a superimposed view of the top and bottom load bearing surfaces, the first direction is substantially nonparallel to all of the one or more directions of the protusions extending along the bottom load bearing surface, and the protrusions are substantially nonuniformly shaped and sized, and each protrusion having a different angle relative to each other.

* * * * *